US006955889B1

(12) United States Patent
Mercolino et al.

(10) Patent No.: US 6,955,889 B1
(45) Date of Patent: Oct. 18, 2005

(54) SIMULTANEOUS DETERMINATION OF FORWARD AND REVERSE ABO BLOOD GROUP

(75) Inventors: Thomas J. Mercolino, Stockton, NJ (US); Kathleen J. Reis, Milford, NJ (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 09/585,820

(22) Filed: Jun. 1, 2000

Related U.S. Application Data

(60) Provisional application No. 60/138,136, filed on Jun. 8, 1999.

(51) Int. Cl.$^7$ .................. G01N 33/555; G01N 33/567; G01N 21/64; G01N 21/82
(52) U.S. Cl. .................. 435/7.25; 435/2; 435/7.2; 435/287.2; 435/288.1; 435/973; 436/501; 436/518; 436/520; 436/523; 436/164; 436/172; 436/177; 436/807; 422/50; 422/58; 422/59; 422/101
(58) Field of Search ................... 435/2, 7.2, 7.25, 435/287.1, 287.2, 288.1, 971, 973, 975; 436/501, 436/503, 518, 520, 523, 164, 172, 177, 800, 436/807; 422/50, 58, 59, 61, 101

(56) References Cited

U.S. PATENT DOCUMENTS

| 2,770,572 | A |   | 11/1956 | Eidon .................. 167/84.5 |
| 2,850,430 | A |   | 9/1958  | Nelson ................. 167/84.5 |
| 3,074,853 | A |   | 1/1963  | Brewer ................. 167/84.5 |
| 3,272,319 | A |   | 9/1966  | Brewer ..................... 206/12 |
| 3,424,558 | A |   | 1/1969  | Eldon ...................... 23/253 |
| 3,502,437 | A |   | 3/1970  | Mass ....................... 23/253 |
| 3,956,477 | A |   | 5/1976  | Price et al. |
| 4,550,017 | A |   | 10/1985 | Liu et al. ................... 424/11 |
| 4,564,598 | A | * | 1/1986  | Briggs ...................... 436/501 |
| 4,584,277 | A |   | 4/1986  | Ullman |
| 4,748,129 | A |   | 5/1988  | Chang et al. ............ 436/519 |

| 5,776,711 | A |   | 7/1998  | Vyas et al. |

FOREIGN PATENT DOCUMENTS

WO          85/01354 A1    3/1985

OTHER PUBLICATIONS

Ashby, J. Exp. Med 29: 267 281 (1918).
Coombs, Brit J Exp. Patho 26:255-266 (1945).
Chung et al., Transf. 33:384-388 (1993).
Lapierre et al., Transf. 30:109-113 (1990).
Scott, Transf. Med. Rev. 5:60-72 (1991).
Growe et al., Transf. Med. Rev. 10:144-151 (1996).
Landsteiner, Science 73:405-409 (1931).
Aminololama-Shakeri S. et al., "Simultaneous ABO and RH Blood Typing by Flow Cytometry Using a Three Color Fluorescence Detection System", Blood, W.B. Saunders, Philadelphia, VA, US, vol. 86, No. 10, Suppl. 01, Nov. 15, 1995, p. 609A DP000983389.
Sharon R. et al, "Quantitative Flow Cytometric Analysis of ABO Red Cell Antigens", Cytometry, Alan R. Liss, Inc. XX, vol. 12, No. 6, 1991, pp. 545-549, XP000983391.
Freedman J et al., "Applications of Flow Cytometry in Transfusion Medicine", Transfusion Medicine Reviews, Grune and Straton, Orlando, FL, US, vol. 9, No. 2, Apr. 1995, pp. 87-109, XP000983392.
Garratty G. et al., "Application of flow Cytofluorometry to Transfusion Science", Transfusion, American Association of Blood Banks, Bethesda, MD, US, vol. 35, No. 2, Jan. 1995, pp. 157-178, XP000983723.
Search Report EP 00 30 4815, dated May 17, 2001.
Morelati, F. et al., "Evaluation fo a new automated instrument for pretransfusion testing", Transfusion, vol. 38, Oct. 1998.

\* cited by examiner

*Primary Examiner*—Christopher L. Chin
*Assistant Examiner*—James L. Grun

(57) ABSTRACT

Simultaneous forward and reverse blood group testing is described using both a visual detection system and a fluorescent based labeling and detection system. Forward and reverse tests could be performed separately, but A and B agglutinates can be detected and discriminated simultaneously.

12 Claims, 9 Drawing Sheets

AB WB | Labeled Reagent Ab & Cells

MIXED ORANGE/GREEN AGGLUTINATES

Orange Max Pixel

Green Max Pixel

SIMULTANEOUS DETERMINATION OF FORWARD AND REVERSE ABO BLOOD GROUP

This application claims the benefit of U.S. Provisional Application No. 60/138,136, filed 8 Jun. 1999.

BACKGROUND OF THE INVENTION

Throughout this application, various patents and papers are referenced. The disclosures thereof in their entireties are hereby incorporated by reference into this application in order to more fully describe the state of the art as known to those skilled therein as of the date of the invention described and claimed herein.

This invention relates to the field of blood group determination, and particularly to the simultaneous determination of forward and reverse blood group testing.

Blood group serology requires the determination of blood cell compatibility between a blood donor and a patient recipient before a transfusion or organ transplant involving the patient. Blood cell compatibility is determined by the non-occurrence of an immunological reaction between antibodies contained in the blood serum of a patient and antigens present on blood cells from the donor.

Many different blood group antigens are found on the surface of the red blood cells of every individual. These antigens, the products of inherited genes, exist in combinations that are likely to be unique between all individuals except identical twins. Blood grouping is generally the process of testing red cells to determine which antigens are present and which are absent, normally utilizing antibodies to the antigen tested for. Additionally, when a person does not have a particular red cell antigen on his or her red blood cells, his or her serum may contain an antibody to that antigen. Whether or not the antibody is present in the serum depends on whether the person's immune system has been previously challenged by, and responded to, that specific antigen or something very similar to it. For example, a person whose red blood cells are Type A, i.e., having "A" antigens on the red cells, will have anti-B antibodies in his or her serum. Thus, if such a person is given type B blood, an immunological reaction will occur with possible serious clinical consequences.

As an additional consideration, it should be noted that the human body is constantly exposed to antigens in pollens, food, bacteria and viruses. Some of these "natural" antigens are apparently so similar to human blood group antigens that they stimulate almost every susceptible person to produce antibodies. Thus, certain antibodies are expected in the serum of anyone whose red cells lack the reciprocal antigen. This is especially true of the ABO system. Accordingly, a second confirmatory test is often performed on the patient/donor sera. The test for expected antibodies of the ABO blood group system in sera is called "reverse" blood grouping.

Antibodies of the ABO blood grouping system are generally immunoglobulin M (IgM). These antibodies have ten antigen binding sites per molecule. The IgM antibody is large enough to span the distance between red blood cells, so that when they are centrifuged, the cells will be bound together in a lattice "cell-antibody-cell-antibody" and will remain clumped together in agglutinates. For example, if anti-A is added to blood group A or blood group AB cells and the mixture is centrifuged, the cells will remain in clumps when resuspended. With the same antibody, group 0 and group B cells will resuspend as individual cells. Agglutination caused by one antibody, such as an IgM antibody, is called direct agglutination.

In transfusion medicine, the most frequently performed test, for the reasons given above, is determination of the ABO blood group. The current state of the art is separately testing for A, B, and sometimes A+B together, antigens on the red cells (forward type); and confirmation (cross-check) testing for anti-A and anti-B antibodies in serum or plasma (reverse type). Thus a minimum of 4 separate tests, but as many as 7 separate tests (A, B, A+B antigens on the sample red cells; anti-A and anti-B in the sample serum/plasma using $A_1, A_2$, B, O reagent red cells) are routinely employed. The results from each of these typing exercises (forward and reverse types) have to agree. Thus, in the U.S. alone approximately 104 million tests are performed annually to determine the blood groups in blood centers.

Since the early 1900's, the general approach known as the "Landsteiner" method, (Landsteiner, Science 73:405 (1931)) together with the work of Ashby, (J. Exp. Med. 29:267 (1919)) and Coombs (Brit. J. Exp. Pathol. 26:255 (1945)), has been to add a patient's red blood cells to a standard laboratory test tube containing a blood group antibody (such as Anti-A or Anti-B), mix to allow antibody/antigen binding reactions to take place, and then to centrifuge. If the antigen tested for is present, the antibody/antigen binding will have taken place resulting in agglutination of the patient's red blood cells. The test tube is manually shaken to dislodge the centrifuged button of "clumped" cells at the bottom. A subjective determination is then made as to whether or not the dislodged cells are "clumped", and to what extent.

During the mid-1900's, attempts were made to simplify this technique to minimize the subjective nature of the test and to reduce mistakes. It was recognized that a somewhat permanent record of the results of compatibility testing could be had by employing wettable, either non-absorbent or in some cases absorbent, test slides or test cards having the requisite immunochemical reagents on at least a portion of their surfaces. In this regard, U.S. Pat. Nos. 2,770,572, 2,850,430, 3,074,853, 3,272,319, 3,424,558, 3,502,437 and 3,666,421 European Patent Application #0 104 881-A2 depict select examples of such test cards and related apparati. The advantages of blood grouping in microplates include easier manipulation of large numbers of samples, objective measurement of agglutination reactions using instruments and computer interfacing for compilation and management of results. A number of expensive and dedicated systems with computer-controlled robotics and high throughput spectrophotometric readers have been introduced for blood bank automation (Chung, et al., Transfusion 33:384 (1992)).

Commercial blood typing kits have been introduced with improved detection of red cell antigen and antibody reactions in special microtubes filled with reagents in gel form. (Lapierre, et al., Transfusion 30:109 (1990)). Utility of solid phase techniques to overcome the inherent problems in the use of hemagglutination as an end point for blood grouping was reviewed by Scott (Transfusion Med. Rev. 5:60 (1991)). Recently Growe et al. (Transfusion Med. Rev. 10:44 (1996)) reported the implementation and use of automated grouping of RBC antigen and serum antibody screening procedures applicable not only to blood centers but also for hospital transfusion laboratories. At least seven different wells with specific typing reagents have to be used in these methods for determining the blood group of a sample. All of the procedures used for large scale blood grouping essentially employed the agglutination based methods and also for the determination of only one antigen or antibody type in a single tube/well. Separately identifiable reactions using fluorescent labeled reagents have also been reported for blood typing applications in the U.S. Pat. Nos. 4,550,017 and 4,748,129.

Current procedures utilize agglutination of red cells as an endpoint. As discussed hereinabove, this is accomplished in test tubes, on slide surfaces, in microplates and in column agglutination tests. The latter 2 methods may be performed manually or by automated instrumentation. All methods require separation of serum (or plasma) from cells to perform both forward and reverse type.

It is therefore of interest to develop a method that performs both forward and reverse type in a single test, while preferably avoiding the need to separate the blood sample prior to testing. Such a method would make it possible for a blood bank technologist to simultaneously determine blood group antigens on red cells as well as antibodies of clinical significance in serum. Such a method would considerably decrease the number of individual tests performed i.e., provide a reduction of about 50 to 100 million tests per year in the number of tests performed in blood centers resulting in significant savings of time and cost. We have developed techniques to allow discrimination of the sample red blood cells (RBCs) from reagent RBCs so that their agglutinates are distinct. Additionally, the novel methods disclosed herein use labeled typing antibody reagent to distinguish their reaction from preformed antibody in the sample. The inventive tests are done without the need to separate the blood sample and thus can be done on whole blood (WB). The tests disclosed herein can be used on automated instruments, where further advantage is gained by not having to separate cells from serum. Further, the simultaneous detection of forward and reverse test reduces the number of tests required to type and confirm the type (forward & reverse test).

In the fluorescent labeling embodiment of the invention, in the forward test, the monoclonal antibody is labeled. For the reverse test the reagent red cells are labeled. Further advantage rests in the ability to distinguish (visually or via automated reader) mixed red cell populations. For instance, reverse test can be performed in 1 test instead of 2, resulting in a reduction of number of tests performed. A further application is the antibody screen, where a pool of 2 cells could be used together instead of 2 separate tests, resulting in a reduction of number of tests performed.

The ability to color cells for a visual system has applications to existing blood group test platforms using tubes, microplates, slides and Column Agglutination Technology (CAT), and test platforms such as the Vitros™ 250, 750 or 950 (Ortho-Clinical Diagnostics, Inc., Rochester, N.Y.) slide method.

Vyas et al. In U.S. Pat. No. 5,776,711 disclose a "simultaneous" ABO and RH(D) blood typing or antibody screening method. However, while similarly attempting to reduce the number of tests to perform an ABO blood group, the instant invention simultaneous performs the samples' red cell ABO status as well as presence of antibodies to A and/or B antigens. In addition, the instant invention utilized whole blood rather than separated serum and red cell components. The instant use of labeled reagent red cells also differs from the Vyas et al. use of synthetic beads.

Simultaneous analysis of ABO blood group can be carried out by labeling reagent red blood cells with appropriate fluorochromes and selecting appropriate monoclonal antibodies with fluorochrome labels. The cells and agglutinates can be measured by laser scanning cytometry on a microscope slide or equivalent. The cells on the slide are illuminated by a scanning laser light source. Typically, laser light sources used include blue argon ion lasers and/or red helium-neon lasers. Fluorescence and light scatter can be determined by the use of a Laser Scanning Cytometer (Compucyte, Cambridge, Mass.).

The use of laser scanning cytometry in the simultaneous determination of forward and reverse test is as follows. When a cell or group of cells (agglutinate) is scanned by the laser light beam, the illuminating light is scattered by the cell or group of cells and the intensity of scatter relates to cell (or agglutinate) size and shape. For example, individual red cells scatter less light than small agglutinates which in turn, scatter less light than large agglutinates.

Likewise, when a cell or group of cells (agglutinate) is scanned by the laser light beam, the illuminating light can induce fluorescence from fluorochrome(s) that have been associated with the cell. If a fluorochrome is relatively uniformly associated per cell with reagent red cells, the fluorescence intensity relates to agglutinate size. For example, individual red cells would fluoresce less than small agglutinates which in turn, would fluoresce less than large agglutinates.

Use of the combination of scattered light and fluorescence is more reliable than either parameter alone in discriminating different classes of agglutinates.

In addition to these two parameters, monoclonal antibodies that have been conjugated with a fluorochrome also may be used to label the cells (and agglutinates) of interest. The fluorescence emitted by the cells when excited by the illuminating laser beam yields additional information about the binding of these monoclonal antibodies to cells or agglutinates for distinguishing subpopulations of cells or agglutinates.

Five parameter (forward scatter, side scatter, and three fluorescence channels) dot plot analysis for simultaneous ABO determination is presented in FIGS. 1A–D.

It may be appreciated by those skilled in the art that flow cytometry or fluorescence microscopy could also be used to perform simultaneous analysis of ABO blood group.

In flow cytometry, the cells and agglutinates to be measured are introduced into the center of a fast moving fluid stream and forced to flow single file out of a small diameter orifice at uniform speeds. The particles are hydrodynamically focused to the center of the stream by a surrounding layer of sheath fluid. The cells within the stream pass a measurement station where they are illuminated by a light source and measurements are made at rates of $2.5 \times 10^2$ to $10^6$ cells per minute. Laser light sources are used in the measurement of cells; typical laser light sources used include argon ion lasers (UV, blue and green light), krypton lasers (yellow and red light), helium-cadmium lasers (UV and blue light), and helium-neon lasers (red light). Fluorescence and light scatter can be determined by the use of a flow cytometer, for example, the CytoronAbsolute™ Flow Cytometer (Ortho-Clinical Diagnostics, Inc., Raritan, N.J.).

In fluorescence microscopy, the cells and agglutinates to be measured are read on a microscope slide or equivalent. The cells are typically illuminated by a white light source or a substantially monochromatic light source. Here, too, laser light sources may be used as the source of the monochromatic light. The presence of agglutinates may be assessed with the white light, and the associated fluorescence assessed with the monochromatic light and appropriate filters. Visual or automated reading may be used for one or both of these readings.

A visual detection technology can also be employed in the forward and reverse blood typing contemplated herein. Such a method, using a column agglutination test (CAT), may employ a BioVue™ cassette (Ortho-Clinical Diagnostics, Inc., Rochester, N.Y.). Such cassette contains columns to which has been added a microparticle matrix. Such matrix can be overlayed with suitable blood typing antibodies dispersed in buffer, forming the initial reaction zone.

CAT can employ automated reader systems to interpret the agglutination result. One such reader is present in the Ortho AutoVue™ (Ortho-Clinical Diagnostics, Inc., Rochester, N.Y.) a fully automated system to perform the CAT. The autoreader is a computerized imaging system consisting of a CCD (charged coupled device) monochrome video camera, and image processing board, and an IBM-compatible PC. The reader first acquires an image of the reaction that is digitised and processed by the image-processing software to extract the reaction features, which are then used by the reaction classification program. These features are used to separate reactions into negative and positive classes, and for translation into one of seven conventional reaction classes or grades. Discriminate analysis, a linear statistical pattern recognition tool, is used to distinguish between negative and weak reactions.

Yet another reader employed in CAT is the BioVue™ Reader 2 (Ortho-Clinical Diagnostics, Inc., Rochester, N.Y.). This Reader has an automated loader for twelve BioVue™ cassettes and has a halogen lamp source and image analysis features permitting cell identification based on RBC wavelength thereby interpreting the agglutination result. Image acquisition is performed by a CCD camera and a digitising board.

SUMMARY OF THE INVENTION

The present invention provides a method of analyzing blood, comprising (a) reacting a sample of blood with anti-A and anti-B antibodies wherein the antibodies are bound to a detectable label; (b) reacting a sample of blood with reagent red blood cells bearing labeled A antigen and labeled B antigen; (c) subjecting the sample to cytometric analysis; and (d) analyzing the cytometry analysis to determine ABO type. The sample of blood can be whole blood and the sample of blood used in steps (a) and (b) above can be the same undivided sample, or can be a different portion of a sample from the same patient. The detectable label bound to the antibodies can be a fluorescent label such as for instance FITC, BODIPY, phycobiliproteins (including phycoerythrin), energy-transfer conjugates of the phycobiliproteins, peridinin chlorophyllin protein, Cascade Blue, AMCA, reactive indocarbocyanine, TRITC, allophycocyanin (APC), phycocyanin (PC), and indodicarbocyanine (Cy5™). Conversely, the labeled A antigen and labeled B antigen can be fluorochromes selected from the group consisting of FITC, BODIPY, phycobiliproteins (including phycoerythrin), energy-transfer conjugates of the phycobiliproteins, peridinin chlorophyllin protein, Cascade Blue, AMCA, reactive indocarbocyanine, TRITC, allophycocyanin (APC), phycocyanin (PC), and indodicarbocyanine (Cy5™).

The invention also contemplates a blood analysis kit comprising (a) a first container having therein labeled anti-A, and anti-B antibodies; and (b) a second container having therein labeled reagent red blood cells bearing labeled group A antigen and labeled group B antigen. The anti-A antibodies can comprise IgM-FITC and the anti-B antibodies can comprise IgM-FITC. The reagent red blood cells are group A1, A2, B and/or O, and may be labeled with fluorochrome selected from the group consisting of reactive dyes (e.g., fluorescein isothiocyanate (FITC), lipophilic dyes, (e.g., merocyanine 540 or $DiIC_{18}(3)$-DS), reactive lipophilic dyes, dyes reacting with membrane structures, and monoclonal antibodies conjugated with fluorescent dyes, the reactivity of these monoclonal antibodies being with a common structure on the red cells (e.g., anti-glycophorin-PE conjugate). Preferably the fluorochrome is $DiIC_{18}(3)$-DS. The kit may additionally comprise a column agglutination technology (CAT) cassette such as a BioVue™ cassette.

The method of the invention is for performing simultaneous forward and reverse ABO type, comprising (a) reacting a sample of blood with anti-A and anti-B antibodies wherein the antibodies are bound to a detectable label; (b) reacting a sample of blood with reagent red blood cells bearing labeled A antigen and labeled B antigen; (c) subjecting the sample to cytometric or fluorescence microscopic analysis; and (d) analyzing the cytometry or fluorescence microscopic analysis to determine ABO type. Further, the method is for the purpose of analyzing blood, comprising (a) reacting a sample of blood with anti-A and anti-B antibodies; (b) reacting a sample of blood with reagent red blood cells bearing A antigen and with reagent red blood cells bearing B antigen; (c) subjecting the sample to visual analysis; and (d) analyzing the visual analysis to determine ABO type. The reagent red blood cells of step (b) can be stained. The method can be performed by column agglutination technology and the results automatically read by an autoreader such as the Ortho AutoVue™ System automated reader or the Ortho BioVue™ Reader 2.

BRIEF DESCRIPTION OF THE DRAWING

FIG. 1A shows the forward x-axis) and side (y-axis) scatter (green max pixel and orange max pixel, respectively) of anti-B FITC and A labeled RBCs with type A whole blood. No events are detected in the side scatter plot in the region of agglutinates. Moreover, no events are available from the side scatter to be further analyzed in the green versus orange plot.

FIG. 1B shows the forward x-axis) and side (y-axis) scatter (green max pixel and orange max pixel, respectively) of anti-B FITC and A labeled RBCs with type B whole blood. Events are detected in the side scatter plot in the region of agglutinates. When these events are further analyzed in the green versus orange plot we confirm the presence of agglutinates of both the reagent cells (orange positive) and of the test rbcs (green positive). Some agglutinates with mixed fluorescence (mixed green and orange) were detected.

FIG. 1C shows the forward (x-axis) and side (y-axis) scatter (green max pixel and orange max pixel, respectively) of anti-B FITC and A labeled RBCs with type AB whole blood. Events are detected in the side scatter plot in the region of agglutinates. When these events are further analyzed in the green versus orange plot we fail to observe agglutinates of the reagent cells (orange positive), but confirm the presence of agglutinates of the test rbcs (green positive). Some agglutinates with mixed fluorescence (mixed green and orange) were detected.

FIG. 1D shows the forward (x-axis) and side (y-axis) scatter (green max pixel and orange max pixel, respectively) of anti-B FITC and A labeled RBCs with type O whole blood. Events are detected in the side scatter plot in the region of agglutinates. When these events are further analyzed in the green versus orange plot we observe agglutinates of the reagent cells (orange positive), but not of the test rbcs (green positive).

FIG. 2 show schematics of the expected results of simultaneous forward and reverse typing.

DETAILED DESCRIPTION OF THE INVENTION

In accordance with the present invention, simultaneous forward and reverse ABO blood group testing will be described in terms of various embodiments. The invention may be used with the column agglutination test (CAT) reaction and separation vessels manufactured and sold in cassette form by Ortho-Clinical Diagnostics, Inc., Rochester, N.Y., under the trademark BIOVUE™. Results can be determined using the AutoVue™ autoreader computerized imaging system, or the BioVue™ Reader 2, both systems described hereinabove.

Other means for carrying out the tests disclosed herein are with tubes, microplates, slides, and test platforms such as the Vitros™ slide method. Results can also be determined using a flow cytometer such as the CytoronAbsolute™ or a laser scanning cytometer or the methods recited hereinabove.

Reagent RBCs typically used for reverse typing have on their surface either $A_1$, $A_2$, B or no ABO antigens (Type $A_1$, Type $A_2$, Type B, Type O). These cells are useful for detecting preformed antibodies which will cause agglutination of the reagent RBCs. For forward type testing, monoclonal anti-A and anti-B are used to detect the presence of their respective antigen on a sample red cell surface.

It is within the teachings of the instant invention to simultaneously determine the presence of other blood group antigens, including, for example, D, C, E, c, e, M, N, S, s, $P_1$, $Le^a$, $Le^b$, K, k, $Js^a$, $Fy^a$, $Fy^b$, $Jk^a$, $Jk^b$, $Lu^a$, and $Lu^b$, and many others. The methods of the instant invention enable fluorescent or visual detection of forward or reverse type blood group testing, and in a preferred embodiment, enable simultaneously forward and reverse blood group testing.

Fluorescent Detection System

In the fluorescent testing embodiment, reagent RBCs, monoclonal anti-A (purified from mouse monoclonal IgM) or anti-B antibody (also purified from mouse monoclonal IgM), or all three, are labeled with fluorescent dye and agglutinates of (1) reagent RBCs with circulating antibody; and (2) monoclonal anti-A or anti-B antibody with RBC surface antigen are detected using a 488 nm laser, for example, using the Compucyte Laser Scanning Cytometer. Alternatively, antisera need not be labeled fluorescently but can be detected by light scatter. The results can further be determined by laser flow cytometry, for example, using the Ortho CytoronAbsolute™ Flow Cytometer. Fluorescence microscopy may also be used.

For simultaneous forward and reverse type, the test was performed wherein the labeled B reagent RBCs were present with the FITC labeled anti-A in the presence of group A WB. See FIGS. 1A and 2A. See Example 1. The FITC-labeled anti-A was able to agglutinate the A red cells in the WB sample resulting in green agglutinates. The preformed anti-B in the plasma of the WB was able to agglutinate the orange labeled reagent B RBCs, resulting in orange agglutinates. Similar tests were performed using B, AB and O WB. See FIGS. 1B–D and 2B–D.

Figure 3:
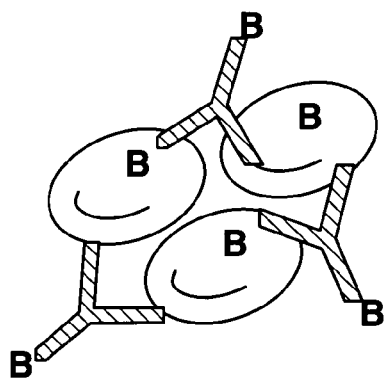
FIG. 3 is a schematic representation of green agglutinates, orange agglutinates, and mixed orange/green agglutinates cross-hatched for color, each of which will present different scatter on the green vs. orange max pixel spectra.
Figure 3:
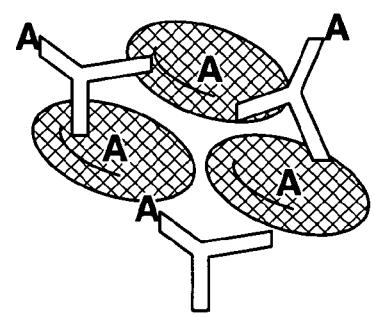
Figure 3:
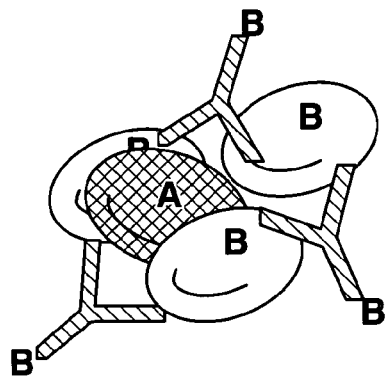
Figure 3:
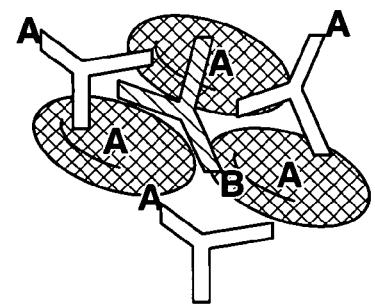
Figure 4:
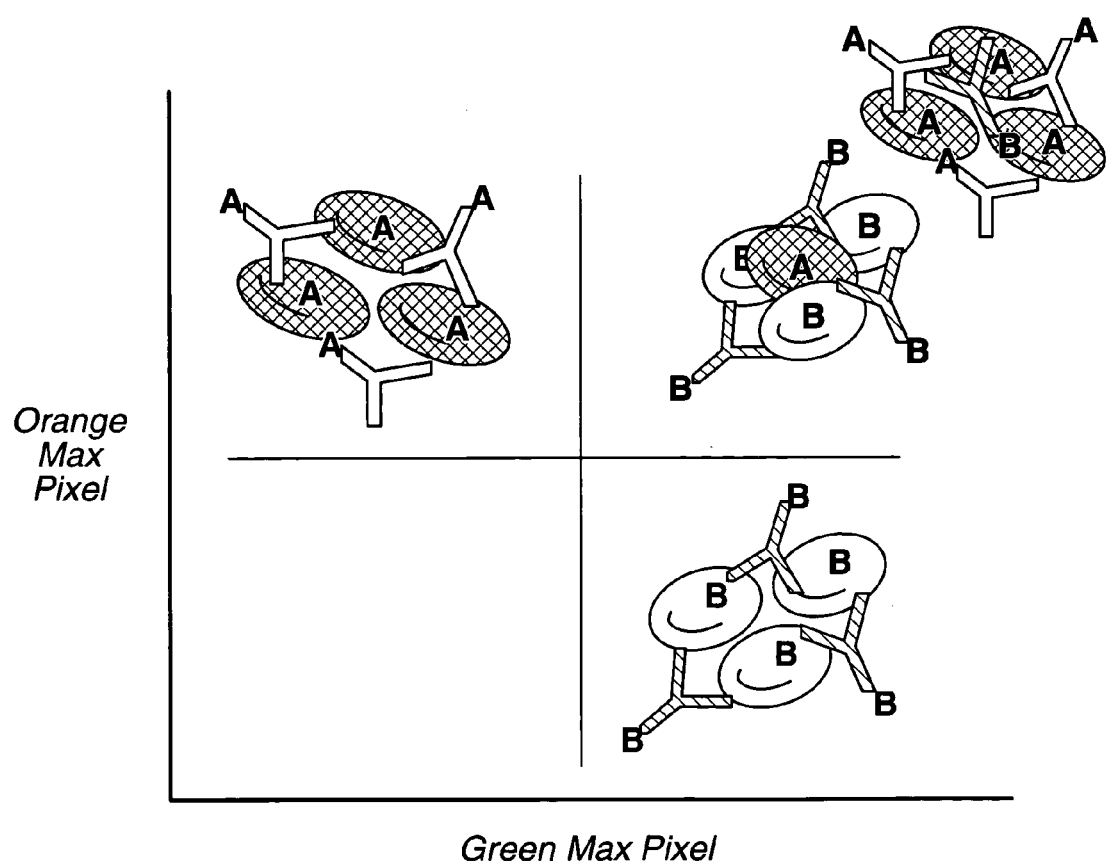
FIG. 4 is a schematic representation of relative position of orange agglutinates, green agglutinates, and mixed orange/green agglutinates cross-hatched for color on the green vs. orange max pixel spectra.
Figure 5:
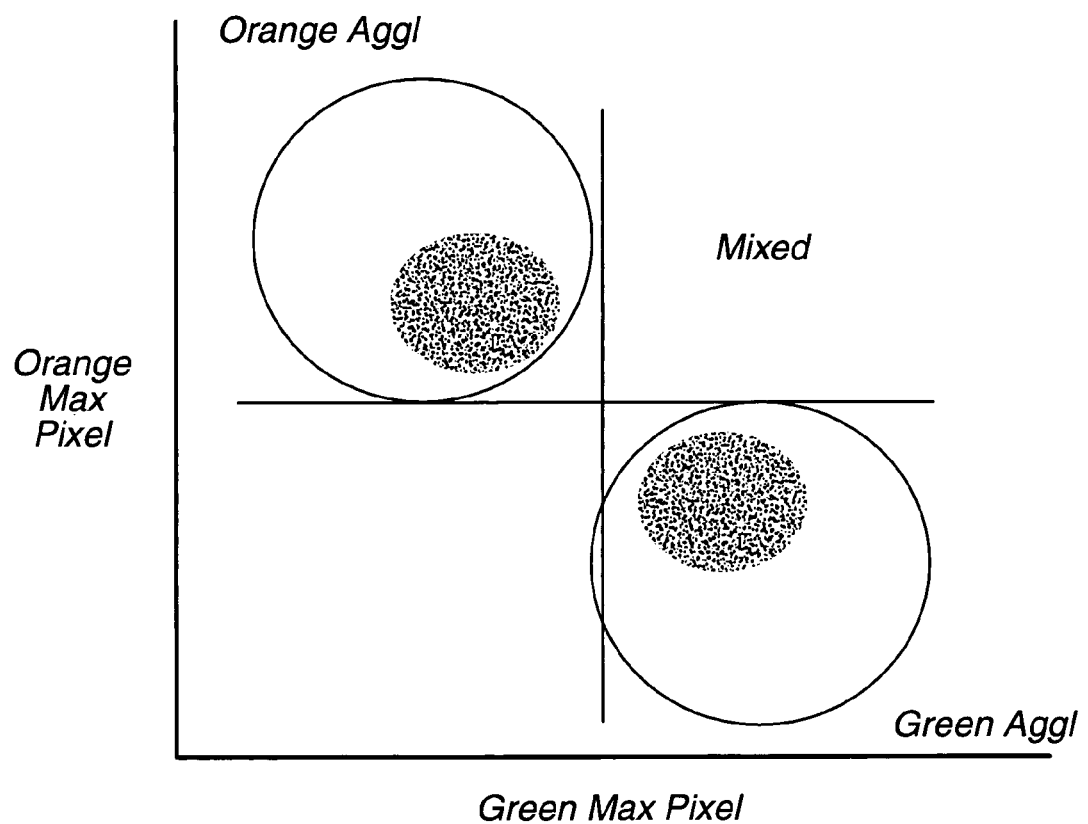
FIG. 5 is a schematic representation of the relative positions (density) of orange agglutinates, green agglutinates and the mixed orange/green agglutinates on the green vs. orange max pixel scatter spectra.

Based on the presence of green and/or orange agglutinates, four distinct patterns of reactivity were observed that correlate with each of the four major ABO blood groups. See Table 1. Thus, in one test, the ABO blood group was determined by simultaneously determining the forward and reverse type. Reciprocally, labeled $A_1$ reagent RBCs and FITC labeled anti-B were admixed in the presence of A, B, AB or O WB. Again, four distinct patterns of agglutination based on the presence of green and/or orange agglutinates were observed, each corresponding to a specific ABO blood group. Thus two tests are performed to determine and confirm the ABO blood group. See Table 1. Some agglutinates with mixed fluorescence (mixed green and orange) were detected. See FIGS. 3–5. These result from trapping/proximity of labeled cells in or near agglutinates of unlabeled cells or alternately trapping or proximity of labeled antibody in or near agglutinates of labeled cells. The presence of the mixed green/orange agglutinates did not interfere with interpretation of results. Representative data sheets for each of the ABO groups using Test 2 are shown in Table 1.

TABLE 1

Reactivity Pattern to Determine and Confirm ABO Blood Group

| WB Sample Group | Test 1 | | Test 2 | |
| --- | --- | --- | --- | --- |
| | FITC anti-A (Green agglut) | Orange Reagent B Cells (Orange agglut) | FITC anti-B (Green agglut) | Orange Reagent $A_1$ Cells (Orange agglut) |
| A | + | + | 0 | 0 |
| B | 0 | 0 | + | + |

TABLE 1-continued

Reactivity Pattern to Determine and Confirm ABO Blood Group

| WB Sample Group | Test 1 | | Test 2 | |
|---|---|---|---|---|
| | FITC anti-A (Green agglut) | Orange Reagent B Cells (Orange agglut) | FITC anti-B (Green agglut) | Orange Reagent A₁ Cells (Orange agglut) |
| AB | + | 0 | + | 0 |
| O | 0 | + | 0 | + |

Results in Table 1 were determined by use of the Compucyte Laser Scanning Cytometer. However, other means for determining agglutinates, with or without need for labeled antisera are contemplated, including but not limited to those methods discussed hereinabove. While the various tests described herein can be done individually, or in any combination thereof, it is the preferred method of the invention to do the forward and reverse tests simultaneously.

Fluorescent dyes are used to label the reagent cells (for reverse type) and the monoclonal anti-A and anti-B antibodies (for forward test). Preferred fluorescent label for labeling reagent cells include 1,1'-dioctadecyl-3,3,3',3'-tetramethylindocarbocyanine-5,5'-disulfonic acid (DiIC$_{18}$(3)-DS). This dye causes the cells to fluoresce orange when excited with a 488 nm blue argon laser light. Other fluorescent labels useful for this embodiment include reactive dyes (e.g., fluorescein isothiocyanate (FITC), lipophilic dyes, (e.g., merocyanine 540), reactive lipophilic dyes (chloromethylbenzamido and methylbenzamido derivatives of DiI, sulfonated derivatives of DiI and sulfonated derivatives of DiO, dyes reacting with membrane structures, and monoclonal antibodies conjugated with fluorescent dyes, the reactivity of these monoclonal antibodies being with a common structure on the red cells (e.g., anti-glycophorin-PE conjugate).

Preferred fluorescent labels for labeling monoclonal antibody include fluorescein isothiocyanate (FITC). The FITC label causes any cells to which this antibody binds to fluoresce green when excited with a 488 nm blue argon laser. FITC is a member of the class of protein-reactive, low molecular weight fluorochrome dyes that may be excited by the 488 nm argon-ion laser, any of which are useful for the monoclonal antibody labeling purposes of the invention. Another example of this class is BODIPY, (Molecular Probes, Eugene, Oreg.), which also will fluoresce green when excited with such laser. Other potentially useful fluorochromes include the phycobiliproteins (e.g., phycoerythrin (PE), energy-transfer conjugates of the phycobiliproteins (e.g., DuoChrome™ (Becton Dickinson, San Jose, Calif.), CY5™ (Ortho-Clinical Diagnostics, Inc., Raritan, N.J.) and others), and peridinin chlorophyllin protein (PerCP™ (Becton Dickinson, San Jose, Calif.). The preceding dyes are all excited by the 488 nm blue argon ion laser, but other combinations of excitation wavelength light source and emitting dye are possible. Some examples include: Cascade Blue and 7-amino-4-methylcoumarin-3-acetic acid (AMCA) with UV excitation; phycoerythrin, reactive indocarbocyanine (Cy3™), and tetramethylrhodamine isothiocyanate (TRITC) with green excitation; allophycocyanin (APC), phycocyanin (PC), and indodicarbocyanine (Cy5™) with red excitation.

Alternatively to the fluorescent test system described, it is not necessary to label the antisera with fluorescent label (FITC). Agglutinates can be detected based on light scatter set at the appropriate settings for particles of this size and type, such as is within the skill of the artisan in this field.

Reverse Test Conditions

In order to optimize the result of the agglutination reaction, it was first determined the working ratio of labeled reagent RBC and labeled monoclonal antibody to whole blood. Thus the readout of the agglutination reaction is maximized and no excess label is utilized. Improvement in specificity is the result of determining the appropriate test ratio since the numbers of false negatives will be reduced.

Labeling of RBCs

For reverse type using DiIC$_{18}$(3)-DS labeled reagent RBC, the desired ratio of reagent RBCs to whole blood was determined based on the ability of that ratio of reagent RBCs to agglutinate with specificity to relative antibody in the WB. In particular, labeled A₁ reagent RBCs were admixed at various ratios with group B whole blood. Tested were 5%, 10% and a 40% reagent RBC suspension to determine a working reagent RBC concentration. A solution of 2 $\mu$M DiI-DS was used. Tagged RBCs were analyzed on the CytoronAbsolute™ Flow Cytometer and mean fluorescence was measured. A concentration of about 5% to about 10% RBC is useful, with about 5% RBC suspension most preferable, since the mean fluorescence was comparably bright using a lower concentration of RBCs. However, a concentration of reagent RBCs that provides sufficiently detectable fluorescence or a detectable number of fluorescent events above background and up to a concentration that is not prohibitive from a standpoint of practicality, e.g., volume of reagent, can be used. Table 2 shows the mean fluorescence obtained with the various ratios of reagent RBCs tested, at the concentration of DiI-DS employed.

TABLE 2

| | Mean Fluorescence |
|---|---|
| Negative Control | 28 |
| 5% RBCs | 75 |
| 10% RBCs | 83 |
| 40% RBCs | 45 |

Range of DiI-DS Concentration

To determine the useful range of DiI-DS concentration for the reverse typing aspect of the invention, five different final concentrations of DiI-DS were tested against the 5% RBC suspension. These cells were analyzed on the CytoronAbsolute™; mean fluorescence and % CV (coefficient of variation) were measured. A concentration of DiI-DS from between 5 micromolar to 40 micromolar tested positive, or any concentration providing a sufficiently bright signal with a percent CV of less than 20% is contemplated in this embodiment. Forty micromolar solution is preferred as possessing the brightest signal with the smallest CV. See Table 3.

TABLE 3

| | Mean Fluorescence | % CV |
|---|---|---|
| 40 $\mu$M | 186 | 7 |
| 20 $\mu$M | 169 | 10 |
| 10 $\mu$M | 138 | 17 |

TABLE 3-continued

|  | Mean Fluorescence | % CV |
|---|---|---|
| 5 μM | 119 | 20 |
| 2 μM | 65 | 35 |
| Negative Control | 28 | 52 |

Reverse Typing—DiI Labeled RBCs & Whole Blood (WB)

Next determined were the conditions where orange labeled group A reagent rbcs agglutinate in group B or O WB, but not in group A or AB WB. Reciprocally, the conditions where labeled B reagent RBCs formed orange agglutinates with group A or O WB, but not with group B or AB WB were determined. Colored agglutinates were measured by relative position of orange and green signal on the max pixel map of the Compucyte Laser Scanning Cytometer using a 488 nm blue argon laser light.

The ratio of WB to labeled RBCs was determined by preparing different combinations and tested using standard blood bank serology techniques. Results were viewed both macroscopically and microscopically. The 5% suspension for WB testing was employed. Agglutination was observed; however, we found the concentration of RBCs in the test mixture was not sufficient to give consistent agglutination results. See Table 4.

TABLE 4

| 5% Group A DiI-DS | WB Volume | Group A WB* | Group O WB |
|---|---|---|---|
| 25 μL | 5 μL | Neg | Pos |
| 25 μL | 25 μL | Neg | Pos |
| 40 μL | 10 μL | Neg | Pos |

*Negative control

The 5% labeled RBC suspension was concentrated to 40% and 5 μL of that was added to 5 μL of WB. Results were favorable, agglutination was observed, and therefore no other ratios were tested.

Forward Typing —FITC Labeled Antibody & Whole Blood

In likewise fashion, for forward type using labeled monoclonal antibodies, the desired ratio of labeled antibody to WB was first determined, based on the ability of that ratio of labeled antibody to agglutinate with specificity to relative cell antigen in the WB. In particular, FITC labeled anti-A was titered with A WB to determine the conditions where green agglutinates form in A or AB WB but not in B or O WB. Reciprocally, then determined were the conditions where labeled anti-B formed green agglutinates with B or AB WB but not with group A or O WB. Colored agglutinates were measured by relative position of orange and green signal on the max pixel map of the Compucyte Laser Scanning Cytometer using a 488 nm blue argon laser light.

Next determined was the ratio of fluorescent label to antibody. Labeled antibody fractions were tested at 3 different dilutions using a 50 μL volume with WB. See Table 5.

TABLE 5

| WB: Vol/Group | FITC Anti-A: Vol/Dil | Reaction Grade |
|---|---|---|
| 10 μL of group A | 50 μL of 1:10 | 2+** |
| 10 μL of group A | 50 μL of 1:100 | 1+ |
| 10 μL of group O* | 50 μL of 1:10 | Neg |
| 10 μL of group O* | 50 μL of 1:100 | Neg |
| 5 μL of group A | 50 μL of 1:50 | 3+ |
| 5 μL of group A | 50 μL of 1:100 | 2+ |

*negative control
**Grading system as defined in AABB Technical Manual, 12$^{th}$ edition; pg 607.

A 1:100 dilution gave the best results using the LSC and was selected for further testing. Based on these results, 50 μL of FITC:antibody was employed for further tests at a 1:100 dilution and 5 μL of DiI-DS labeled RBCs. However, a range of label:antibody to be employed could be any concentration that will produce detectable fluorescence above background (at the low end) and prozone (at the high end).

Visual Detection System

The ability to alter the color of a red cell would allow simultaneous testing of 2 cell populations to be performed visually or spectrophotometrically (by absorbance or reflectance), i.e., without the need to detect fluorescence. For example, red cells exposed to cyanide or azide would be expected to turn from bright red to brown. Red agglutinates could then be detected visually from brown agglutinates. While modifying the intrinsic color of the red cell hemoglobin would be contemplated by this embodiment, simply attaching or otherwise associating chromophores to the red cells could otherwise detectably change their spectral properties.

In the visual detection embodiment, forward and reverse test can be conducted using the column agglutination method (CAT) e.g., by employing the BioVue™ cassette. A forward bloodtyping assay may be conducted utilizing the column agglutination device as herein described by using a columnar device to which has been added the matrix of the invention. A monoclonal antibody or polyclonal antibody containing antiserum is dispersed in a physiologically compatible buffer and added to the matrix of microparticles to immerse them, and extends from the matrix toward the inlet port to form the initial reaction zone. Suitable amounts of such antibodies may be routinely optimized by those skilled in the art, depending generally on the antigenic affinity and specificity of the antibodies. The antibodies are dispersed in a buffer that may also contain suitable additives known to the art to help potentiate their reactivity and prevent non-specific binding, such as high molecular weight polymers, and the like.

Examples of these include polyvinyls, dextran, gelatin, and polyethylene glycol. Lower molecular weight polymers may also be added to increase the density of the solution.

Figure 6:
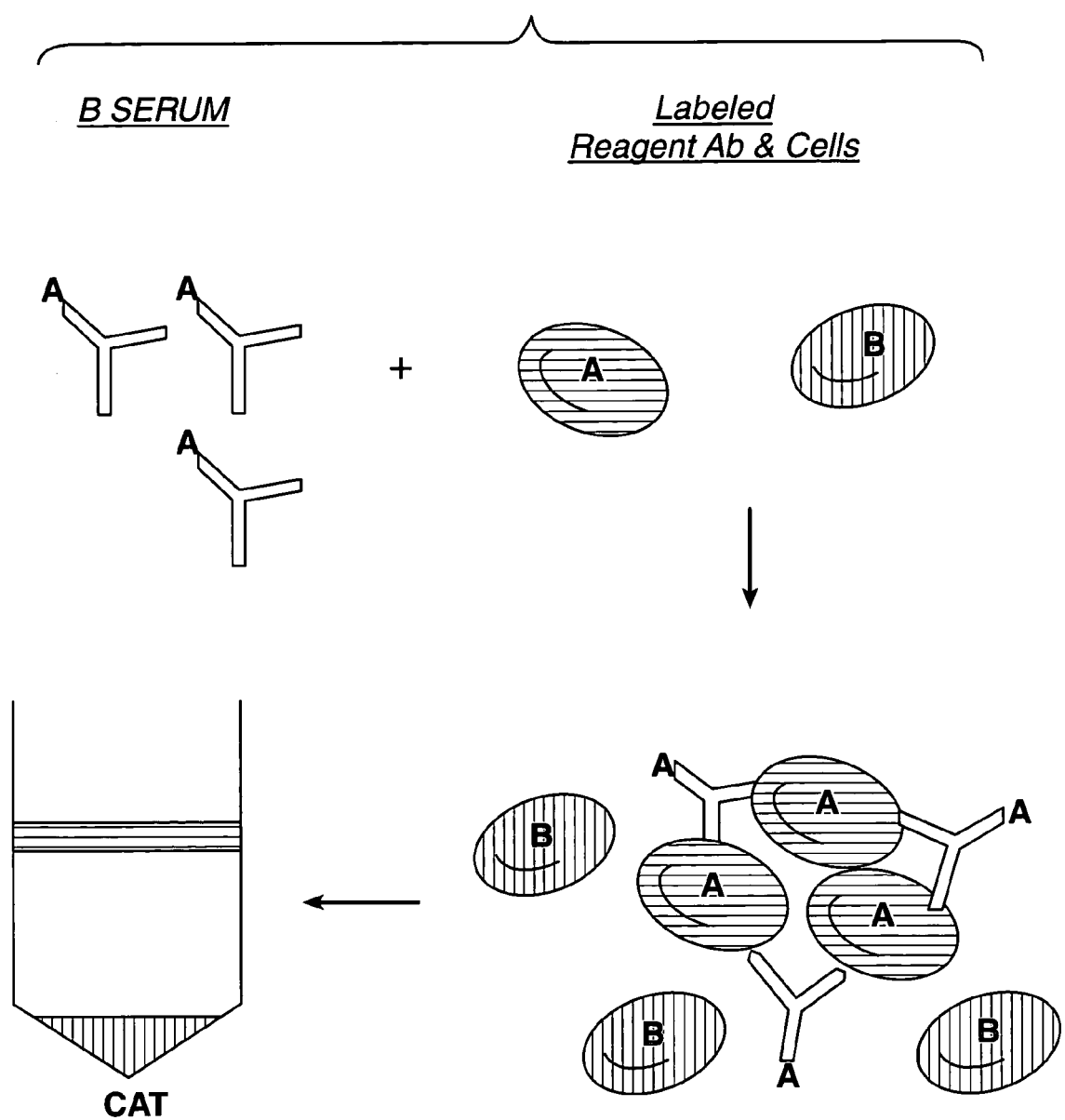
FIG. 6 is a schematic representation of visual detection of reverse testing of B serum in a CAT system. Labeled reagent A and B cells are admixed with B serum, resulting in brown agglutinates which, following centrifugation, are observed at the top of the gel column of the CAT system; the non-reacted labeled reagent B cells are observed at the bottom of the column are cross-hatched for color.

In this illustration, if antibodies to Type B blood cells were added, Type B blood cells contained in the patient's sample will bind to the antibody, forming a layer of aggregated cells trapped near the top portion of the matrix. In this Example, type A cells will not agglutinate, and will be centrifuged to the bottom of the device. Often times, a patient's cells may contain weakly reacting variants. The moderate reaction might be demonstrated by smaller scattered agglutinates throughout the column matrix, while negatives form a button on the bottom of the matrix column. FIG. 6 depicts a reverse testing using the column agglutination method whereby reagent A and B cells are separately labeled. Sample serum is delivered to the top of the column per manufacturer's instructions and the tube incubated and centrifuged in accordance therewith. Reagent A cells agglutinate with anti-A antibody present while the reagent B cells pass to the bottom of the column, indicating the sample serum was type B.

Reagent RBCs (Affirmgen® $A_1$ and B cells, Ortho-Clinical Diagnostics, Raritan, N.J.) were treated with sodium azide ($NaN_3$) at a final concentration of 0.2%. The $NaN_3$ reduces the iron in the hemoglobin resulting in a color change from the typical red to a deep brown or maroon color. Untreated cells from the same Affirmagen lot served as controls. Untreated control and treated test cells were tested independently with group B sera in a BioVue™ Reverse cassette using manufacture's directions (10 μl 3–5% red cells and 40 μl of serum; then centrifuged 5 minutes in a BioVue centrifuge in accordance with manufacturer's instructions). The B sera is expected to agglutinate $A_1$ cells but not the B cells. No differences were observed in the agglutination of the untreated vs. treated cells, except that the untreated cells were red and the treated cells were brown. Refer to Example 2 and Table 6 herein.

Automated determination of agglutination results using the visual detection systems described may be accomplished by use of the AutoVue™ autoreader computerized imaging system, or the BioVue™ Reader 2, both systems described hereinabove.

If visual observation of agglutinates is desired, as disclosed herein, it is preferable to first stain any colorless cells or colorless particles adhering to cells with a dye suitable to effect a visually perceptible agglutination reaction. The hemoglobin of red blood cells provides such a suitable color naturally, without staining. Direct agglutination studies may be performed on ABO red blood cells as illustrated above, as well as those blood cells containing D, C, E, c, e, M, N, S, s, $P_1$, $Le^a$, $Le^b$, K, k, $Js^a$, $Fy^a$, $Fy^b$, $Jk^a$, $Jk^b$, $Lu^a$ and $Lu^b$ antigens, and the like. Similarly, when sera are to be tested for the presence of antibodies to a particular antigen or cell containing an antigen, they can be mixed with known antigens. If the unknown serum contains antibodies to the known antigen that is provided, the reactants will be agglutinated and trapped when they move onto or down through the matrix, while negative serum will not effect a reaction, and agglutinates will not be trapped.

The methods of the invention have been illustrated in great detail for use in a blood serology context. However, it should be understood that it is within the contemplation of the invention to conduct simultaneous forward and reverse type binding assays involving any binding ligands associated with particles, such that the particles will react as a result of the binding of the ligands to their binding partners in both a forward and reverse fashion. For example, the "antibody screen" test, which is routinely performed using plasma or serum that has been separated from the sample RBC's, could be performed using whole blood with labeled reagent red cells used as disclosed here. Alternatively, serum or plasma could be used but the number of tests required to perform an antibody screen or antibody identification could be reduced by 50% by mixing 1 unlabeled reagent red cell and 1 labeled reagent red cell. Although red blood cell forward and reverse typing system is illustrated, one skilled in the art will appreciate that other systems may be optimized in this manner.

The following examples are provided for purposes of illustration only and not by way of limitation of the scope of the invention.

EXAMPLE 1

Fluorescent Detection Embodiment

Part A—Reagent Preparation

A stock solution of the lipophilic, fluorescent membrane label, 1,1'-dioctadecyl-3,3,3',3'-tetramethylindocarbocyanine-5,5'-disulfonic acid (DiI-DS) (Molecular Probes Inc., Eugene, Oreg.) was prepared by adding 1 mL of ethanol (Sigma, St Louis Mo.) to a 1 mg vial of DiI-DS and mixing vigorously, resulting in a 1 mg/mL concentration. The stock solution can be stored at room temperature up to 6 months protected from the light.

A working solution of DiI-DS was prepared by diluting the stock solution with Hanks Balanced Salt Solution (HBSS)(Sigma) to a concentration of 80 μM. Unused working solution was discarded.

Part B—Red Blood Cell (RBC) Fluorescent Labeling

Whole blood was collected in Vacutainer adenine citrate dextrose (ACD) preservative tubes (Becton-Dickinson, Franklin Lakes, N.J.) from human donors whose blood group types were A1, B and O. RBCs were separated by centrifugation at approximately 3000×g for 5 minutes and washed twice in 3 to 5 ml phosphate buffered saline (PBS) (Gibco) and centrifuged at approximately 3000×g for 3 to 5 minutes after each wash. A 5% RBC suspension was prepared using HBSS as the diluent.

Equal volumes (0.1 to 5 ml) of 5% RBC suspension and DiI-DS working solution were combined in a test tube and incubated at 37° C. for 30 minutes, protected from the light. Tubes were briefly agitated manually every ten minutes. Labeled RBCs were washed three times in 3 to 5 ml PBS, centrifuged at approximately 3000×g for 5 minutes and resuspended in HBSS to make a 5% solution.

Orange fluorescence was confirmed on the CytoronAbsolute™ Flow Cytometer using Immunocount II™ software (Ortho-Clinical Diagnostics, Inc., Raritan, N.J.).

RBCs were gated based on light scatter parameters and fluorescence associated with gated RBC's was measured. Measurement of fluorescence above background indicated sufficient labeling. A negative control of identical RBCs incubated with an equal volume of PBS (0.1 to 5 ml) instead of fluorescent label was run in parallel.

Part C—Fluorescein Isothiocyanate(FITC) Labeling of Antibody

Mouse monoclonal anti-A, clone MH04, and mouse monoclonal anti-B, clone NB10.5A5, were obtained in tissue culture form from the Ortho-Clinical Diagnostics, Inc. manufacturing facility. The monoclonal antibodies were partially purified and concentrated using standard methods.

Purified anti-A and anti-B were dialyzed in carbonate buffer, pH 9.5, and labeled with FITC according to standard protocols. The FITC-labeled antibodies were separated from free FITC using size exclusion chromatography. The absorbance of individual fractions at 280 nm and 492 nm was determined. The F/P (fluorescein/protein) molar ratio for each fraction was calculated using the following formula:

$$F = A495/0.15$$

$$P = [A280 - (A495 \times 0.32)]/1.2$$

$$F/P \text{ ratio} = (F/P) \times 2.39$$

The three fractions with the highest F/P ratio were used in the fluorescent simultaneous forward and reverse testing embodiments of the invention.

| Anti-A Fractions | F/P Ratio | Anti-B Fractions | F/P Ratio |
|---|---|---|---|
| 3 | 20 | 3 | 36 |
| 4 | 26 | 4 | 20 |
| 5 | 32 | 5 | 12 |

Part D—Simultaneous Forward/Reverse Typing in Whole Blood (WB) and Test Interpretation—Laser Scanning Cytometer (LSC)

We prepared DiI-DS A labeled RBCs diluted in the anti-B FITC labeled antibody. Antibody was diluted to 1:100 in 0.5 ml PBS with 2% bovine serum albumin and 1% sodium azide. Nine volumes of the diluted antibody were mixed with one volume of labeled cells. Fify-five µL of the labeled cells/antibody mixture was added to 5 µL of WB as follows in Sub-parts 1 through 4. Tubes were centrifuged for 15 seconds at approximately 3500 rpm in a Clay-Adams (Parsippany, N.J.) serofuge. RBCs were gently resuspended. Slides were prepared by adding 3 µL of the reaction mixture to 7 µL of PBS, then applying a coverslip.

Slides were analyzed using the LSC (Compucyte, Cambridge, Mass.).

Sub-Part 1

Figure 1:
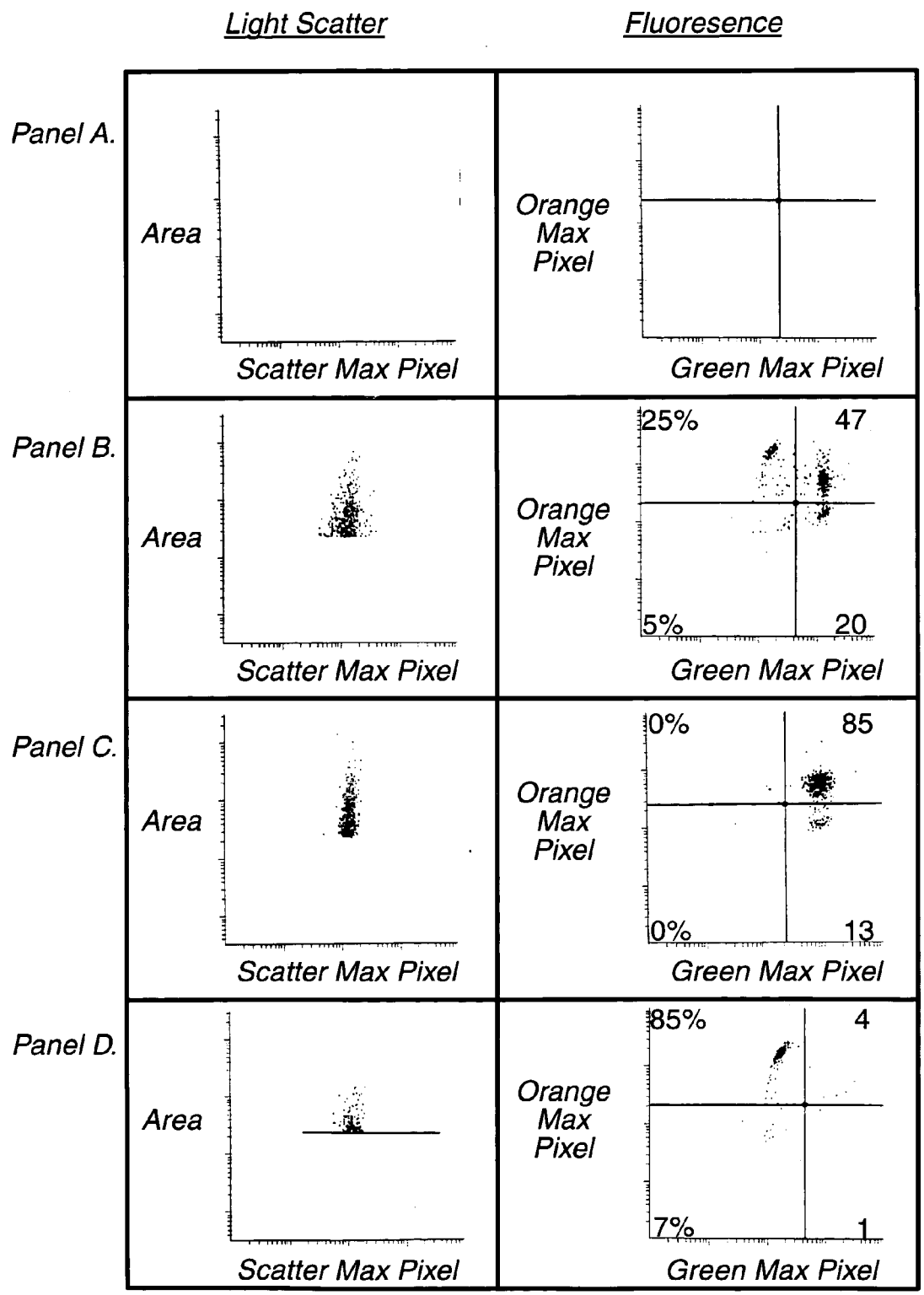
FIG. 1 shows graphic representations of four color laser scanning cytometric analysis of simultaneous forward and reverse ABO blood group typing.
Figure 2A:
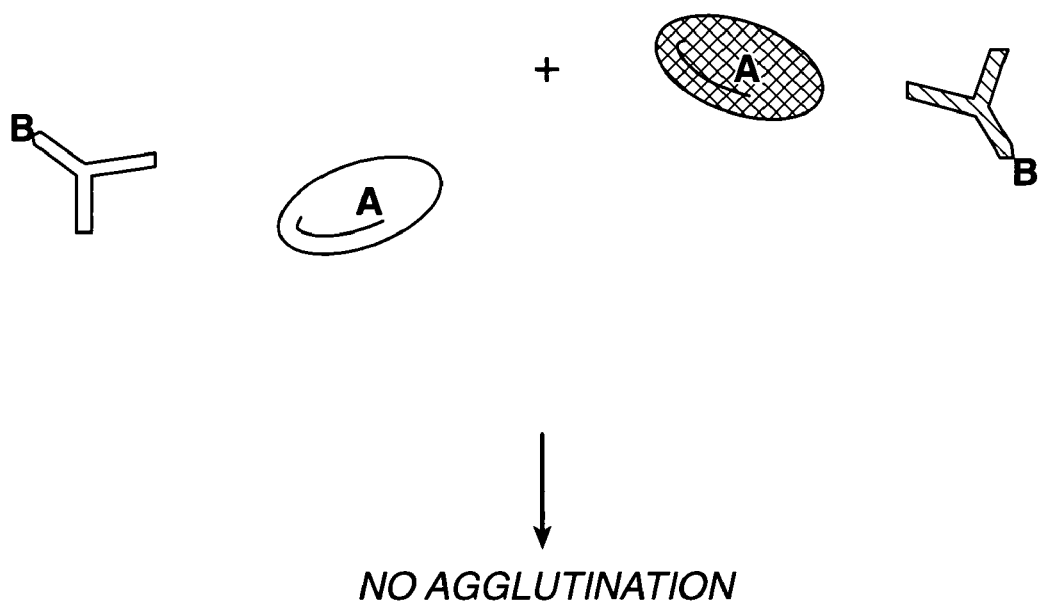
FIG. 2A shows that admixture of labeled A reagent RBCs and labeled anti-B with type A whole blood results in no agglutination cross-hatched for color.
Figure 2B:
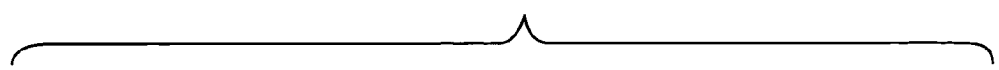
FIG. 2B is a schematic representation of the admixture of labeled A reagent RBCs and labeled anti-B, with type B whole blood, resulting in agglutinates of B RBCs—with anti-B (green) and anti-A—A reagent cells (orange) cross-hatched for color.
Figure 2B:
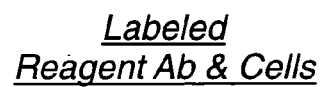
Figure 2B:
Figure 2B:
Figure 2B:
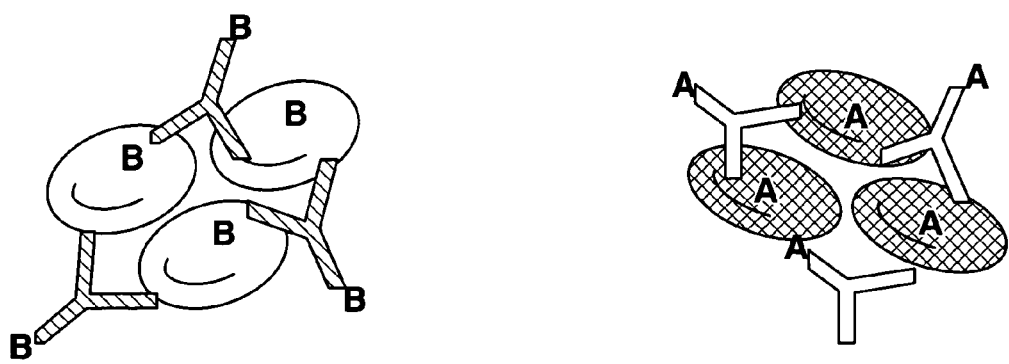
Figure 2C:
FIG. 2C is a schematic representation of the admixture of labeled A reagent RBCs, and labeled anti-B with type AB whole blood, resulting in agglutinates of AB RBC—anti-B (green) cross-hatched for color.
Figure 2C:
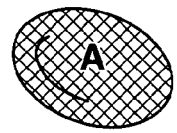
Figure 2C:
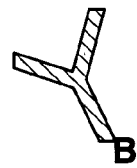
Figure 2C:
Figure 2C:
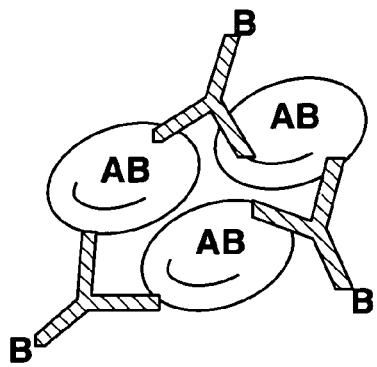
Figure 2D:
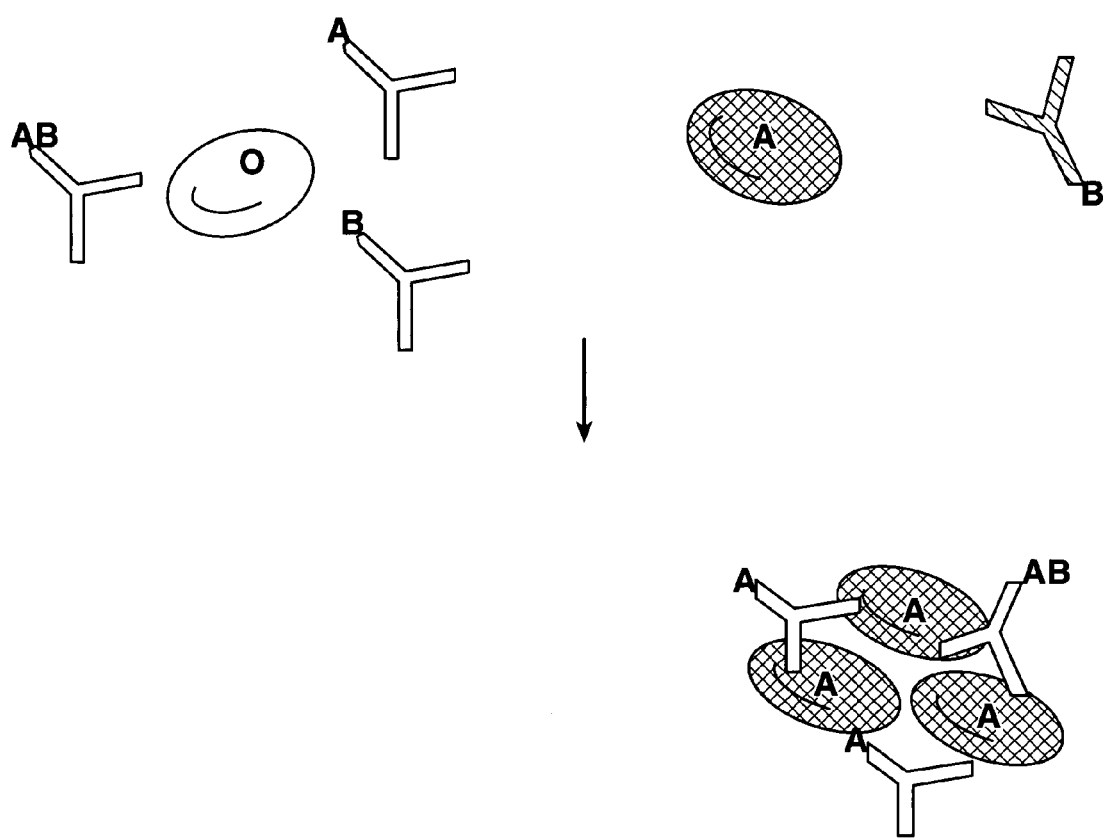
FIG. 2D is a schematic representation of the admixture of labeled A reagent RBCs and labeled anti-B, with type O whole blood, resulting in agglutinates of anti-A—A reagent cells (orange) cross-hatched for color.

Using the materials and procedures of Part D herein, Type A whole blood was employed. Since A whole blood contains no antibodies to A red cells, no agglutinates should form with the labeled reagent red cells. Additionally, since type A whole blood cells do not bear the B antigen, no agglutinates should form with the anti-B FITC. FIG. 1A shows the forward (x-axis) and side (y-axis) scatter (green max pixel and orange max pixel, respectively) of anti-B FITC and A labeled RBCs with type A whole blood. As predicted no events are detected in the side scatter plot in the region of agglutinates. Moreover, no events are available from the side scatter to be further analyzed in the green versus orange plot.

Sub-Part 2

Using the materials and procedures of Part D herein, Type B whole blood was next tested. Since B whole blood contains antibodies to A red cells, agglutinates should form with the labeled reagent red cells. Additionally, since type B whole blood cells express the B antigen, agglutinates should form with the anti-B FITC. FIG. 1B shows the forward (x-axis) and side (y-axis) scatter (green max pixel and orange max pixel, respectively) of anti-B FITC and A labeled RBCs with type B whole blood. Events are detected in the side scatter plot in the region of agglutinates. As predicted, when these events are further analyzed in the green versus orange plot we confirm the presence of agglutinates of both the reagent cells (orange positive) and of the test RBCs (green positive).

Sub-Part 3

Using the materials and procedures of Part D herein, Type AB whole blood was next tested. Since AB whole blood contains no antibodies to A red cells, no agglutinates should form with the labeled reagent red cells. However, since type AB whole blood cells express the B antigen, agglutinates should form with the anti-B FITC. FIG. 1C shows the forward (x-axis) and side (y-axis) scatter (green max pixel and orange max pixel, respectively) of anti-B FITC and A labeled RBCs with type AB whole blood. Events are detected in the side scatter plot in the region of agglutinates. As predicted, when these events are further analyzed in the green versus orange plot we fail to observe agglutinates of the reagent cells (orange positive), but confirm the presence of agglutinates of the test RBCs (green positive).

Sub-Part 4

Finally, using the materials and procedures of Part D herein, Type O whole blood was tested. Since O whole blood contains antibodies to A red cells, agglutinates should form with the labeled reagent red cells. However, since type O whole blood cells do not express the B antigen, no agglutinates should form with the anti-B FITC. FIG. 1D shows the forward (x-axis) and side (y-axis) scatter (green max pixel and orange max pixel, respectively) of anti-B FITC and A labeled RBCs with type O whole blood. Events are detected in the side scatter plot in the region of agglutinates. As predicted, when these events are further analyzed in the green versus orange plot we observe agglutinates of the reagent cells (orange positive), but not of the test RBCs rbcs (green positive).

EXAMPLE 2

Visual Detection Embodiment

Part A—Preparation of Colored Red Cells

Commercial preparations of Group $A_1$ and B red cells (Affirmagen®) were obtained from Ortho-Clinical Diagnostics, Inc. (Raritan, N.J.). Two 1-mL aliquots of Group $A_1$ RBCs were removed from the vial and placed in a separate tube. One aliquot was admixed with 20 µl of 10% $NaN_3$ (Mallinckrodt, Paris, Ky.). The other aliquot was untreated and served as a control. Each tube was capped and the contents incubated for 16 hours at ambient temperature. After overnight treatment, the $NaN_3$-treated RBC appeared brown in color, while the untreated control cells remained red.

Part B—Reverse Bio Vue Column Testing—Dual Column Test

Sodium azide treated cells were tested in a standard BioVue™ Reverse Cassette using 10 µl of A1 cells plus 40 µl of group B sera in one column and 10 µl of B cells plus 40 µl of group B sera in a different column (columns 3 and 4 in Table 6). Control cells, untreated A1 and B cells, were tested in columns 1 and 2, respectively. Following centrifugation in accordance with manufacturer's instructions, agglutinated A1 cells, both untreated control cells (column 1) and treated test cells (column 3) were observed at the top of the bead column indicating the presence of anti-A in the group B sera. Unagglutinated B cells, both untreated control cells (column 2) and treated test cells (column 4) were observed at the bottom of the column indicating the absence of anti-B. The untreated control cells were red in appearance and the treated test cells appeared brown. These results indicated that the treatment of the A1 and B cells did not impair their ability to agglutinate in the bead column.

Part C—Reverse BioVue Column Testing—Single Column Test

In Example 2, Part B, A1 and B cells were tested in individual columns to determine the reverse group of the sample. Next, in one column, we combined 10 µl of A1 untreated cells (red) and 10 µl of B treated cells (brown) with 40 µl of group B sera. Following centrifugation, 2 distinct cell populations were observed. Agglutinated (A1) cells were observed at the top of the bead column and unagglutinated brown (B) cells were observed at the bottom of the column (column 5 in table 6). The results indicated that the correct reverse group could be determined in 1 column (1 test) instead of the normal 2 columns. Reciprocally, 10 µl treated $A_1$ cells and 10 µl untreated B cells were tested in accordance with Part B herein and the results were able to detect agglutinated brown ($A_1$) cells and unagglutinated red (B) cells (column 6 in table 6).

The results from Parts B and C hereof are shown in Table 6. See FIG. 6.

TABLE 6

Visual detection and discrimination of 2 distinct cell populations

| | BioVue Reverse Column Number | | | | | |
|---|---|---|---|---|---|---|
| | 1 | 2 | 3 | 4 | 5 | 6 |
| RBC (10 µl each) | $A_1$ untr | B untr | $A_1$ tr | B tr | $A_1$ untr + B tr | $A_1$ tr + B untr |
| Reaction observed following centrifugation | 4+ | 0 | 4+ | 0 | 3–4+ mixed | 3–4+ mixed |
| Description | Red cells on top of bead column | Red cells at bottom of bead column | Brown cells at top of bead column | Brown cells at bottom of bead column | Red cells at top and brown cells at bottom of bead column. Few cells scattered in the column. | Brown cells at top and red cells at bottom of bead column. Few cells scattered in the column. |

Note: all columns contained 40 µl of B sera in addition red cells indicated.
untr, untreated control cells
tr, $NaN_3$ treated cells

What is claimed is:

1. A method of analyzing ABO blood type in a reverse test, comprising:
   (a) admixing a sample of blood with first reagent red blood cells bearing A antigen and with second reagent red blood cells bearing B antigen, wherein said admixing is performed in a single column;
   (b) incubating the admixture under conditions sufficient for agglutination to occur;
   (c) subjecting the incubated admixture in the single column to visual or automated computerized imaging analysis to determine agglutination of said first and/or second reagent red blood cells or lack thereof; and
   (d) analyzing the visual or automated computerized imaging analysis of agglutination to determine ABO reverse type.

2. The method of claim 1 wherein one of said first or second reagent red blood cells of step (a) are distinguishably stained.

3. The method of claim 2 wherein the single column subjected to visual or automated computerized imaging analysis is selected from the group consisting of tube and column agglutination technology.

4. The method of claim 3 wherein the column agglutination technology is a column agglutination test reaction and separation vessel in cassette form.

5. The method of claim 4 wherein agglutination is determined with the automated computerized imaging system.

6. The method of claim 1 wherein the sample of blood is serum or plasma.

7. A method of simultaneous antibody testing of a blood sample using two cell populations, comprising:
   (a) admixing a sample of blood with a first group of reagent red blood cells bearing a first antigen and a second group of reagent red blood cells bearing a second antigen, wherein one group of said reagent red blood cells are distinguishably stained, and wherein said admixing is performed in a single column;
   (b) incubating the admixture under conditions sufficient for agglutination to occur;
   (c) subjecting the incubated admixture in the single column to visual or automated computerized imaging analysis to determine agglutination of said first and/or second group of reagent red blood cells or lack thereof; and
   (d) analyzing the visual or automated computerized imaging analysis of agglutination to determine anti-first and/or second antigen antibodies in the sample.

8. The method of claim 7 wherein the sample of blood is serum or plasma.

9. The method of claim 7 wherein the single column subjected to visual or automated computerized imaging analysis is selected from the group consisting of tube and column agglutination technology.

10. The method of claim 9 wherein the column agglutination technology is a column agglutination test reaction and separation vessel in cassette form.

11. The method of claim 10 wherein agglutination is determined with the automated computerized imaging system.

12. The method of claim 7 wherein the first and second groups of reagent red blood cells are independently selected from groups A1, A2, B, O, D, C, E, c, e, M, N, S, s, P1, Lea, Leb, K, k, Jsa, Fya, Fyb, Jka, Jkb, Lua, or Lub.

* * * * *